(12) United States Patent
Jiang et al.

(10) Patent No.: US 10,086,184 B2
(45) Date of Patent: Oct. 2, 2018

(54) METHOD OF MANUFACTURING PERCUTANEOUS PORTS WITH WIRE COILS

(71) Applicant: ALFRED E. MANN FOUNDATION FOR SCIENTIFIC RESEARCH, Santa Clarita, CA (US)

(72) Inventors: Guangqiang Jiang, Irvine, CA (US); Tom He, Canyon Country, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 532 days.

(21) Appl. No.: 14/877,857

(22) Filed: Oct. 7, 2015

(65) Prior Publication Data

US 2016/0101274 A1    Apr. 14, 2016

Related U.S. Application Data

(60) Provisional application No. 62/061,588, filed on Oct. 8, 2014.

(51) Int. Cl.
```
A61M 39/02      (2006.01)
B21F 3/04       (2006.01)
B21F 15/00      (2006.01)
B23K 1/00       (2006.01)
C23F 1/14       (2006.01)
```

(52) U.S. Cl.
CPC ........ *A61M 39/02* (2013.01); *A61M 39/0247* (2013.01); *B21F 3/04* (2013.01); *B21F 15/00* (2013.01); *B23K 1/0006* (2013.01); *B23K 1/0008* (2013.01); *C23F 1/14* (2013.01); *A61M 2039/0258* (2013.01); *A61M 2039/0261* (2013.01); *A61M 2207/00* (2013.01); *Y10T 29/49826* (2015.01)

(58) Field of Classification Search
CPC ....... B21B 45/0275; B21H 1/06; B08B 3/123; C23C 8/24; C21D 1/72; C21D 9/40; C21D 1/06; C21D 1/74; C21D 8/10; F16G 5/16; B21D 53/14; Y10T 29/49819
See application file for complete search history.

(56) References Cited

U.S. PATENT DOCUMENTS

| | | |
|---|---|---|
| 3,752,162 A | 8/1973 | Newash |
| 3,783,868 A | 1/1974 | Bokros |

(Continued)

OTHER PUBLICATIONS

Jiang, International Search Report and Written Opinion, PCTUS2015054753, dated Jan. 25, 2016, 11 pgs.

(Continued)

*Primary Examiner* — Sarang Afzali
*Assistant Examiner* — Ruth G Hidalgo-Hernandez
(74) *Attorney, Agent, or Firm* — Morgan, Lewis & Bockius LLP

(57) ABSTRACT

The various implementations described herein include methods used to manufacture a percutaneous port for promoting tissue in-growth around the percutaneous port. In one aspect, the method includes providing a tubular structure having an outer surface and providing a coil having an outer surface and comprised of a plurality of loops. The method further includes joining at least a portion of the outer surface of the coil to the outer surface of the tubular structure.

17 Claims, 14 Drawing Sheets

(56) References Cited

U.S. PATENT DOCUMENTS

| | | | |
|---|---|---|---|
| 3,815,577 A | 6/1974 | Bucalo | |
| 4,038,703 A * | 8/1977 | Bokros | A61F 2/06 623/2.38 |
| 4,854,316 A | 8/1989 | Davis | |
| 5,700,241 A | 12/1997 | Goodman | |
| 6,379,816 B1 | 4/2002 | De Loose et al. | |
| 6,471,689 B1 | 10/2002 | Joseph et al. | |
| 7,635,383 B2 | 12/2009 | Gumm | |
| 7,704,225 B2 | 4/2010 | Kantrowitz | |
| 8,956,394 B1 | 2/2015 | McDonnell | |
| 2003/0236575 A1 | 12/2003 | Yu et al. | |
| 2004/0006396 A1 | 1/2004 | Ricci et al. | |
| 2005/0004526 A1 | 1/2005 | Reinemann | |
| 2006/0047249 A1 | 3/2006 | Shubayev et al. | |
| 2007/0060891 A1 | 3/2007 | Skiera et al. | |
| 2007/0299392 A1 | 12/2007 | Beyar et al. | |
| 2009/0157014 A1 | 6/2009 | Osborne et al. | |
| 2009/0171376 A1 | 7/2009 | Burton et al. | |
| 2009/0192464 A1 | 7/2009 | Axelsson et al. | |
| 2010/0042070 A1 | 2/2010 | Gill et al. | |
| 2011/0029002 A1 | 2/2011 | Mann et al. | |
| 2011/0144417 A1 | 6/2011 | Jagger et al. | |
| 2011/0178540 A1 | 7/2011 | Axelsson et al. | |
| 2011/0313359 A1 | 12/2011 | Cohen | |
| 2012/0089121 A1 | 4/2012 | Lee et al. | |
| 2012/0123197 A1 | 5/2012 | Woodruff et al. | |
| 2012/0143141 A1 | 6/2012 | Verkaik et al. | |
| 2012/0172819 A1 | 7/2012 | Dugrot | |
| 2012/0203318 A1 | 8/2012 | Mann et al. | |
| 2013/0267914 A1 | 10/2013 | Batiste et al. | |
| 2013/0338599 A1 | 12/2013 | Kaylor | |
| 2014/0052085 A1 | 2/2014 | Johansson et al. | |
| 2014/0066895 A1 | 3/2014 | Kipperman | |
| 2014/0121629 A1 | 5/2014 | Macaulay et al. | |
| 2014/0236123 A1 | 8/2014 | Birmingham et al. | |
| 2015/0051708 A1 | 2/2015 | Anderson | |
| 2015/0126962 A1 | 5/2015 | Freeman et al. | |
| 2015/0250513 A1 | 9/2015 | De Lavigne Sainte Suzanne | |
| 2016/0101275 A1 | 4/2016 | Jiang et al. | |

OTHER PUBLICATIONS

Jiang, Communication Pursuant to Rules 161(1) and 162, EP15787760.6, Jun. 12, 2017, 2 pgs.

Jiang, Communication Pursuant to Rules 161(1) and 162, EP15787761.4, Jun. 12, 2017, 2 pgs.

Jiang, Office Action, U.S. Appl. No. 14/877,865, dated Jun. 16, 2017, 16 pgs.

Jiang, International Search Report and Written Opinion, PCTUS2015054751, dated Jan. 25, 2016, 11 pgs.

* cited by examiner

METHOD OF MANUFACTURING PERCUTANEOUS PORTS WITH WIRE COILS

RELATED APPLICATIONS

This application claims priority to U.S. Provisional Application No. 62/061,588, filed Oct. 8, 2014, the contents of which are incorporated herein by reference in its entirety.

TECHNICAL FIELD

The disclosed embodiments relate generally to a medical device, and more particularly to a percutaneous port with wire coils that promote tissue in-growth around the port.

BACKGROUND

Modern medicine often requires prolonged or repeated access to the interior of a patient's body. For example, treatment of a patient may require access to a patient's vascular system to, for example, provide therapeutic agents thereto and/or remove fluids therefrom.

Continuous access to the interior of a patient's body may be provided through a port surgically implanted through the patient's skin. These ports are otherwise known as percutaneous ports.

Conventional percutaneous ports, however, often result in poor tissue integration around the surface of the port, which can lead to infection and even inadvertent port removal.

Accordingly, there is a need to provide a percutaneous port that better integrates with the surrounding tissue.

SUMMARY

According to some embodiments, a percutaneous port is manufactured by joining at least a portion of the outer surface of a coil to the outer surface of a tubular structure. More specifically, some embodiments include a method of manufacturing a percutaneous port for promoting tissue in-growth around the percutaneous port by providing a tubular structure having an outer surface, and providing a coil having an outer surface and comprised of a plurality of loops. The method further includes joining at least a portion of the outer surface of the coil to the outer surface of the tubular structure.

In some embodiments, the method further comprises winding the coil around the tubular structure in a spiral, prior to the joining.

In some embodiments, the joining comprises brazing at least a portion of the outer surface of the coil to the outer surface of the tubular structure. Furthermore, in some embodiments, brazing is performed for a predefined period of time that is based at least in part on a thickness of the wire comprising the coil, a thickness of the outer surface of the tubular structure, and a predefined brazing temperature.

In some embodiments, the outer surface of the tubular structure comprises a plated material, and the coil comprises a coil material, wherein the plated material and the coil material are chemically reactive with one another.

In some embodiments, the coil comprises a material selected from the group consisting of titanium and its alloys, nitinol, tungsten and its alloys, molybdenum and its alloys, niobium and its alloys, cobalt-chromium based alloys, noble metals, such as platinum, iridium, palladium, silver, gold, and their alloys, and medical grade stainless steel.

In some embodiments, the tubular structure is made from titanium, and the outer surface of the tubular structure is made from nickel.

In some embodiments, the coil is formed by providing a center rod, winding a wire around the center rod, and removing the center rod. Furthermore, in some embodiments, removing the center rod occurs after joining at least a portion of the outer surface of the coil to the outer surface of the tubular structure. In some embodiments, removing the center rod includes etching away the center rod using a chemical etchant. Furthermore, in some embodiments, the center rod is selected from the group consisting of molybdenum and tungsten, and the chemical etchant is selected from the group consisting of sodium phosphate, aqueous ferric chloride, an aqueous ferricyanide ion solution, a soluble molybdate, and a soluble tungstate.

In some embodiments, the method further comprises providing an additional coil having an outer surface and comprised of a plurality of loops and winding the additional coil around the tubular structure in a spiral. At least a portion of the outer surface of the additional coil is joined to the outer surface of the tubular structure, the loops of the coil having a first diameter and the loops of the additional coil having a second diameter, wherein the first diameter is significantly larger than the second diameter. In some embodiments, the additional coil is interleaved between the coils.

In some embodiments, the longitudinal axis of the coil is substantially parallel to the longitudinal axis of the tubular structure.

In some embodiments, after joining, at least some of the loops of the coil are oriented at an angle to the outer surface of the tubular structure. Furthermore, in some embodiments, the angle to the outer surface of the tubular structure is substantially perpendicular. Moreover, in some embodiments, the at least some of the loops of the coil are further oriented at an angle substantially parallel to the longitudinal axis of tubular structure.

In some embodiments, a predefined spacing between adjacent loops in the coil is variable.

In some embodiments, the tubular structure is cylindrical, while in other embodiments, the tubular structure is not cylindrical.

Another aspect includes the percutaneous port for promoting tissue in-growth around the percutaneous port, which comprises a tubular structure having an outer surface, and a coil having an outer surface and comprised of a plurality of loops, wherein at least a portion of the outer surface of the coil is joined to the outer surface of the tubular structure.

In some embodiments, a cross section of the tubular structure is circular, square, rectangular, or polygonal.

In some embodiments, the coil forms a spiral around the tubular structure. Furthermore, some embodiments further include an additional coil having an outer surface and comprised of a plurality of loops, wherein the additional coil also forms a spiral around the tubular structure. In such embodiments, the plurality of loops of the coil has a substantially larger diameter than the plurality of loops of the additional coil. Furthermore, in some embodiments, the spiral formed by the additional coil is interleaved with the spiral formed by the coil.

In some embodiments, after joining, at least some of the plurality of loops are oriented so as to form an angle with the outer surface of the tubular structure.

In some embodiments, the at least a portion of the outer surface of the coil is brazed to the outer surface of the tubular structure.

In some embodiments, the outer surface of the tubular structure comprises a plated material, and the coil comprises a coil material, wherein the plated material and the coil material are chemically reactive with one another.

In some embodiments, the coil comprises a material selected from the group consisting of titanium and its alloys, nitinol, tungsten and its alloys, molybdenum and its alloys, niobium and its alloys, cobalt-chromium based alloys, noble metals, such as platinum, iridium, palladium, silver, gold, and their alloys, and medical grade stainless steel.

In some embodiments, the tubular structure is made from titanium.

In some embodiments, the outer surface of the tubular structure is made from nickel.

In yet another aspect, a percutaneous port for promoting tissue in-growth around the percutaneous port comprises a plate having opposing substantially flat first and second surfaces, wherein the plate defines a hole there through, and a coil having an outer surface and comprised of a plurality of loops, wherein at least a portion of the outer surface of the coil is joined to the first surface of the plate around the hole.

In some embodiments, the plate is circular, square, rectangular, or polygonal shaped.

In some embodiments, the coil forms a spiral around the hole of the plate. Furthermore, in some embodiments, the percutaneous port further comprises an additional coil having an outer surface and comprised of a plurality of loops, wherein the additional coil forms an additional spiral around the hole of the plate. The spiral has a first spiral diameter, and the additional spiral has a second spiral diameter distinct from the first spiral diameter. Furthermore, the plurality of loops of the coil have a first loop diameter, and the plurality of loops of the additional coil has a second loop diameter distinct from the first loop diameter. In some embodiments, the spiral formed by the coil is interleaved with the additional spiral formed by the additional coil.

In some embodiments, after joining, at least some of the plurality of loops are oriented so as to form an angle with the first surface of the plate.

In some embodiments, the at least a portion of the outer surface of the coil is brazed to the first surface of the plate. Furthermore, in some embodiments, the first surface of the plate comprises a plated material, and the coil comprises a coil material, wherein the plated material and the coil material are chemically reactive with one another.

In some embodiments, the coil comprises a material selected from the group consisting of: titanium and its alloys; nickel and its alloys; nitinol; medical-grade stainless steel; silver; and noble metals including platinum, gold, iridium, and their alloys.

In some embodiments, the plate is made from titanium.

In some embodiments, the first surface of the plate is made from nickel.

Numerous details are described herein in order to provide a thorough understanding of the example implementations illustrated in the accompanying drawings. However, some embodiments may be practiced without many of the specific details, and the scope of the claims is only limited by those features and aspects specifically recited in the claims. Furthermore, well-known methods, components, and circuits have not been described in exhaustive detail so as not to unnecessarily obscure more pertinent aspects of the implementations described herein.

The embodiments described herein offer significant advantages over traditional techniques and designs. For example, conventional ports use mesh-like textures on the outside surface of the ports. These designs do not adequately penetrate into surrounding tissue, and poorly integrate with a patient's body, thereby increasing the risk of port removal and infection. Unlike conventional ports, the embodiments disclosed herein (e.g., that include coils), facilitate a deeper depth of penetration into surrounding tissue, for more effective, robust, and longer lasting tissue in-growth. As such, the percutaneous ports described herein are strongly anchored to the surrounding tissue, thereby greatly reducing the risk of port removal and infection.

BRIEF DESCRIPTION OF THE DRAWINGS

So that the present disclosure can be better understood, a detailed description is provided below that makes reference to features of various embodiments, some of which are illustrated in the appended drawings. The appended drawings, however, merely illustrate the more pertinent features of the present disclosure and are not intended to limit the scope of the invention.

Figure 1A:
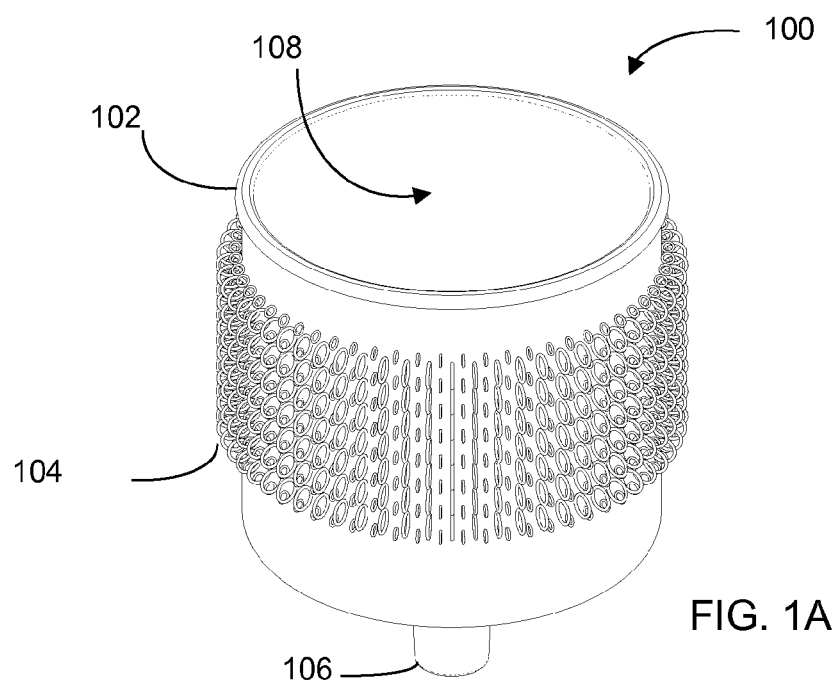
FIG. 1A is an oblique view of an embodiment of a percutaneous port.

In accordance with common practice the various features illustrated in the drawings may not be drawn to scale. In addition, some of the drawings may not depict all of the components of a given method or apparatus. Finally, like reference numerals may be used to denote like features throughout the specification and figures.

DETAILED DESCRIPTION

The following is a detailed description of various embodiments of percutaneous ports and their method of manufacture.

Figure 1B:
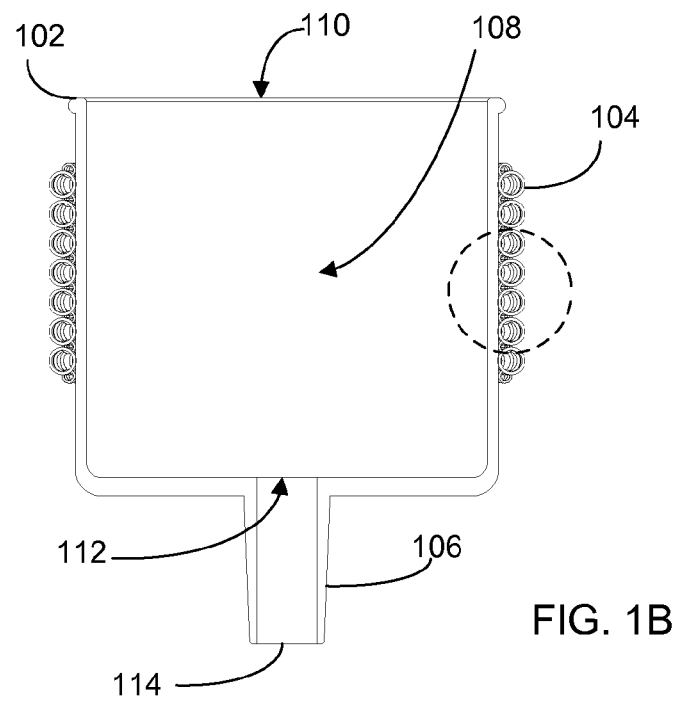
FIG. 1B is a side cross-sectional view of the percutaneous port shown in FIG. 1A.
Figure 1C:
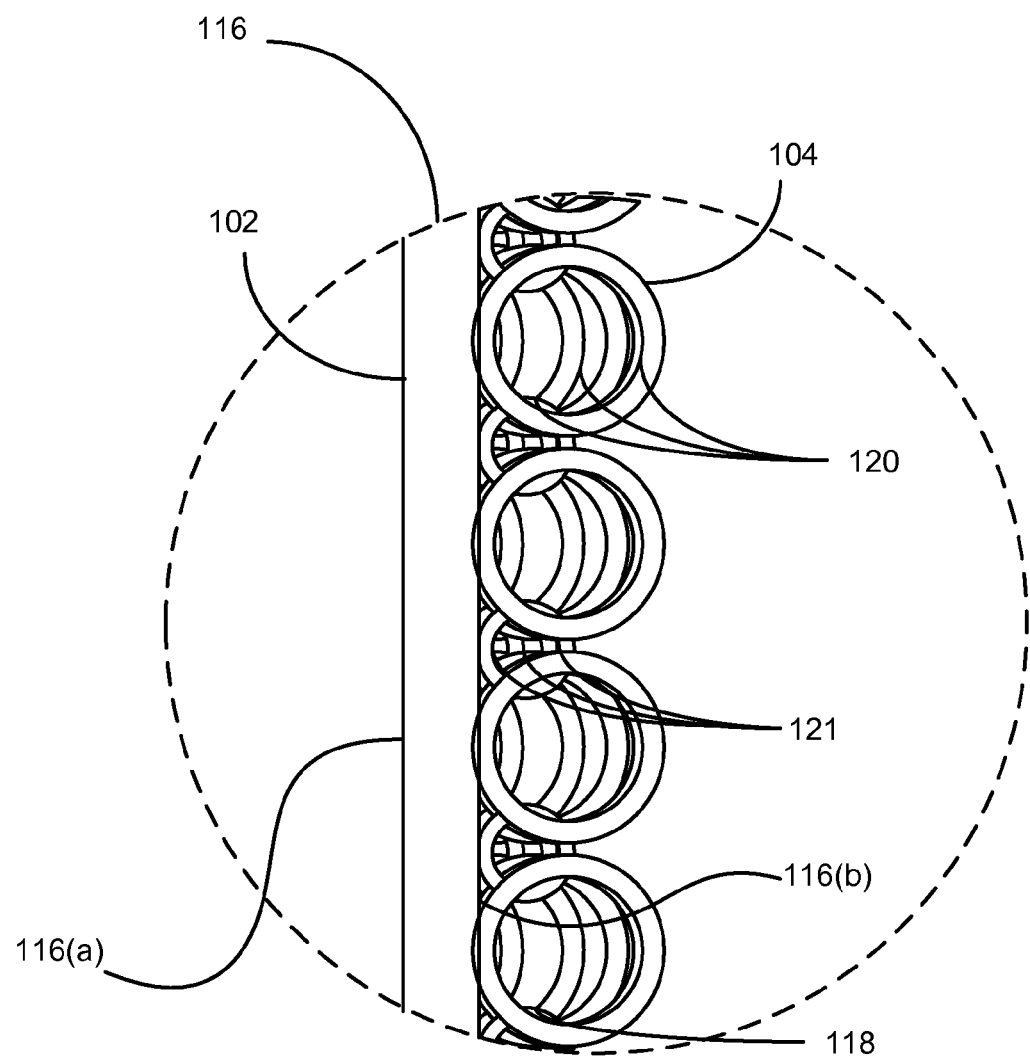
FIG. 1C is a close-up of the cross-sectional view shown in FIG. 1B.

FIGS. 1A-1C illustrate multiple views of a percutaneous port 100 in accordance with some embodiments. Specifically, FIG. 1A is a perspective view of an embodiment of a percutaneous port 100; FIG. 1B is a side cross-sectional view of the percutaneous port 100 shown in FIG. 1A; and FIG. 1C is a close-up of the cross-sectional view shown in FIG. 1B.

The percutaneous port 100 includes a tubular structure 102, coils 104, and optionally, an additional tubular structure 106. More specifically, the tubular structure 102 is formed from a wall 116 that encloses a cavity or chamber 108. In some embodiments, the wall 116 has a thickness of between 0.1-25.4 mm. The wall 116 has an inner surface 116(a) and an outer surface 116(b) (best seen in FIG. 1C). As explained below, the coils 104 are joined to the outer surface 116(b).

As shown in FIG. 1B, in some embodiments, the percutaneous port 100 further forms a first opening 110 and a second opening 112. In some embodiments, these openings 110, 112 are disposed opposite to one another. In some embodiments, the first opening 110 is significantly larger than the second opening 112.

In some embodiments, an additional tubular structure 106 is coupled to the tubular structure 102, as shown in FIG. 1B. The additional tubular structure 106 is formed from a wall that encloses an additional cavity or chamber. In some embodiments, the wall of the additional tubular structure 106 has the same thickness as the wall 116 of the tubular structure 102, while in other embodiments it has a tapering thickness as shown. In some embodiments, the additional tubular structure 106 shares an opening 112 with tubular structure 102, and has an opening 114 opposite to the opening 112.

In some embodiments, the additional tubular structure 106 enables deeper penetration of the port into the tissue of a subject or patient, while also defining an additional chamber for further isolating outside contaminants from reaching the subject, thus better preventing infection.

In embodiments that include both the tubular structure 102 and the additional tubular structure 106, the percutaneous port 100 forms a funnel from the wider opening 110 to the narrower opening 114. In these embodiments, a diameter (or equivalent dimension) of the tubular structure 102 is significantly larger than a diameter (or equivalent dimension) of the additional tubular structure 106. In some embodiments, the diameter (or equivalent dimension) of the tubular structure 102 is between 1.0-50.8 mm, and the diameter (or equivalent dimension) of the additional tubular structure 106 is between 0.1-20 mm.

The tubular structure 102 and/or the additional tubular structure 106 have any suitable shape. While FIGS. 1A-1C illustrate a tubular structure 102 that has a cylindrical shape and circular cross-section, any other suitable shapes may be employed. For example, in other embodiments, the cross-sectional shape of the tubular structure 102 and/or the additional tubular structure 106 taken along a plane perpendicular to their longitudinal directions, may be circular, square, rectangular, hexagonal, or polygonal. Moreover, the diameter (or equivalent dimension) of the tubular structure 102 and/or the additional tubular structure 106 may taper along the longitudinal axis like a funnel.

In some embodiments, the tubular structure 102 and/or the additional tubular structure 106 is made from a material selected from the group consisting of: titanium and its alloys, nitinol, tungsten and its alloys, molybdenum and its alloys, niobium and its alloys, cobalt-chromium based alloys, noble metals, such as platinum, iridium, palladium, silver, gold, and their alloys, cobalt-chromium alloys, medical grade stainless steel, zirconia, alumina and their composites, and other biocompatible metallic or ceramic materials. In some embodiments, the outer surface 116 of the tubular structure 102 is plated with a brazing material used for joining the coils 104 to the tubular structure 102, a process described in greater detail below. Furthermore, in some embodiments, the outer surface 116 of the tubular structure 102 comprises a material selected from the group of materials that can be used to join the coils to the tubular structure and form biocompatible structure. They consist of: nickel, gold and nickel and titanium alloys and nickel and titanium in the forms of laminates, pastes or thin films.

The coil 104 includes multiple individual loops, coils, or windings 120, as best seen in FIG. 1C. At least a portion of the coil 104 is joined to at least a portion of the outer surface 116 of the tubular structure 102 using any suitable technique, such as brazing. In some embodiments, the coil 104 has loops with a diameter of between 104-5000 um.

In some embodiments, at least a portion of an additional coil 118 is joined to at least a portion of the outer surface 116 of the tubular structure 102, as shown, using any suitable technique, such as brazing. As was the case with the coil 104, the additional coil also has multiple loops, coils or windings 121. In some embodiments, the additional coil 118 is continuous, while in other embodiments, the additional coil 118 includes multiple spaced apart sections (not shown).

In some embodiments, the coils 104 and/or 118 are continuous, while in other embodiments, the coils 104 and/or 118 includes multiple spaced apart sections (not shown). In some embodiments, for example, a plurality of individual, unconnected rings for joining to the outer surface 116 of the tubular structure 102 is provided. In some embodiments, the coils 104 and/or 118 are wound around the tubular structure 102 in a spiral or larger coil, as shown. In other embodiments, the coils 104 and/or 118 is joined to the tubular structure 102 in any other suitable configuration, such as multiple parallel coils with longitudinal axes that are parallel to the longitudinal axis of the tubular structure, i.e., coils 104 and/or 118 are arranged such that the coils 104 and/or 118 are substantially parallel to the longitudinal axis of the tubular structure 102.

In some embodiments, the coils 104 and/or 118 have distinct loop diameters from one another, form distinct spirals around the tubular structure 102. In these embodiments, as shown in FIGS. 1A-1C, the distinct spirals formed by the coil 104 and the additional coil 118 are interleaved with one another. Furthermore, in some embodiments, as shown in FIG. 1C, a coil at least partially overlaps with an additional coil such that the plurality of loops of the coil is interleaved with the plurality of loops of the additional coil.

In some embodiments, the loops of the additional coil 118 have a diameter substantially smaller than the diameter of the coil 104. For example, as illustrated in FIG. 1C, the loops 120 of a coil 104 have a distinct loop diameter (e.g., 1000 um) that is substantially larger than the loop diameter of the loops 121 (e.g., 300 um) of the additional coil 118. In some embodiments, the additional coil 118 has loops with a diameter between 25-1250 um. The loops 120, 121 can be formed into variety of suitable shapes, including, but not limited to, a circle, square, rectangle, or polygon.

As the loop diameter determines the depth of penetration into the surrounding tissue, the loop diameter for a respective plurality of loops is determined based on the type of tissue in-growth intended for the respective plurality of loops. For example, a smaller loop diameter (e.g., 25 to 300 um) allows better tissue in-growth with the dermis and epidermis, thus forming a better seal and reducing infection rates at the skin. In contrast, a larger loop diameter (e.g., 200 to 1000 um) allows deeper penetration and better tissue in-growth with surrounding tissue, enabling stronger mechanical integration and thus better mitigating issues of inadvertent port removal and exit site infection. Therefore, in some embodiments, such as that shown, two distinct loop diameters are used together.

In some embodiments, each loop of a coil 104, 118 has a loop diameter distinct from the loop diameter of adjacent loops within the same coil 104, 118. For example, the loop diameter of successive loops 120 of a coil 104 alternates between 1000 um and 300 um.

In some embodiments, the additional coil 118 is wound around the tubular structure 102 between each winding of the coil 104, as shown. In some embodiments, the additional coil 118 is also joined to the coil 104 using any suitable technique, such as brazing.

In some embodiments, the coils 104, 118 are made from a material selected from the group consisting of: titanium and its alloys, nitinol, tungsten and its alloys, molybdenum and its alloys, niobium and its alloys, cobalt-chromium based alloys, noble metals, such as platinum, iridium, palladium, silver, gold, and their alloys, and medical grade stainless steel. Furthermore, in some embodiments, the material of the coils 104 is chemically reactive with the material of the outer surface 116 of the tubular structure 102.

In some embodiments, each loop of a coil 104, 118 has a predefined spacing or pitch from adjacent loops in the respective coil 104. The predefined spacing or pitch determines the density of loops in a respective coil (e.g., a number of loops for a fixed length of a coil). For example, a coil having a length of 50 mm and a predefined spacing of 0.5 mm between loops, will have a greater number (and thus, a greater density) of loops than a different coil having the same length, but a larger predefined spacing of 1 mm between loops. Increasing the density of loops in a respective coil 104 by adjusting the predefined spacing between the respective loops 118 enables improved tissue in-growth, as each additional loop provides an additional anchor point for surrounding tissue and thus creates a stronger mechanical integration of the percutaneous port 100. However, too small a pitch could prevent adequate tissue in-growth. In some embodiments, the predefined spacing between adjacent loops in a respective coil 104 is variable (e.g., the predefined spacing between successive loops 118 alternates between 0.5 mm and 1 mm), while in other embodiments, the predefined spacing is uniform (e.g., the predefined spacing between successive loops 118 is 0.5 um).

In some embodiments, the loops 118, 120 are oriented at an angle to the outer surface 116 of the tubular structure 102. For example, as illustrated in FIGS. 1A-1C, the loops 118, 120 are oriented at an angle substantially perpendicular to the outer surface 116 of the tubular structure 102. Optionally, in some embodiments, the loops 118, 120 are oriented so as to form two or more distinct angles. In a non-limiting example, successive loops 118 in a respective coil 104 are oriented such that they form angles which alternate between a 45 degree angle and a 135 degree angle. In some embodiments, the loops 118, 120 are further oriented such that the longitudinal axis of the loops are substantially parallel (i.e., vertically, as shown in FIGS. 1A-1C), or alternatively, substantially perpendicular (i.e., horizontally), to the longitudinal axis of the tubular structure 102. In these embodiments, referring to the perspective shown in FIG. 1B, the longitudinal axis is defined as the axis running from the top (e.g., first port 110) of the tubular structure 102 to the bottom (e.g., second port 112).

As described in greater detail below, the plurality of loops of the coil 104 and/or additional coil 118 facilitates optimal tissue in-growth around the port 100, enabling a stronger physical integration of the port 100 to the patient's tissue thereby mitigating issues such as inadvertent port removal and infection.

The percutaneous port 100 provides an interface enabling internal access to a patient into which the percutaneous port 100 is implanted. In particular, the tubular structure 102, in combination with at least the first opening 110 and the second opening 112, define a conduit (e.g., chamber 108) through which external components (e.g., electronic controller or fluid pump) can access internal components (e.g., implanted sensors or the vascular system) of the patient. For example, when surgically implanted into a subject (not shown), the percutaneous port 100 serves as a physical access port for catheters (e.g., drug or material delivery), cables (e.g., for power or signal transport), and/or other external or internal components and/or devices. Use of the percutaneous port eliminates the need for subsequent surgical procedures for accessing the internal systems within a patient.

During a surgical procedure, the percutaneous port 100 is implanted into a patient in such a way that the loops of the coils 104, 118 penetrate into and are positioned between the tubular structure 102 and the surrounding tissue. As the subject recovers from the procedure, new tissue grows through a lattice formed by the loops of the coils 104, 118 thereby securely anchoring the port to the surrounding tissue. This greatly reduces inadvertent removal and repositioning of the percutaneous port 100, reduces irritation and infection at the surgical site, and shortens the recovery time.

Figure 2A:
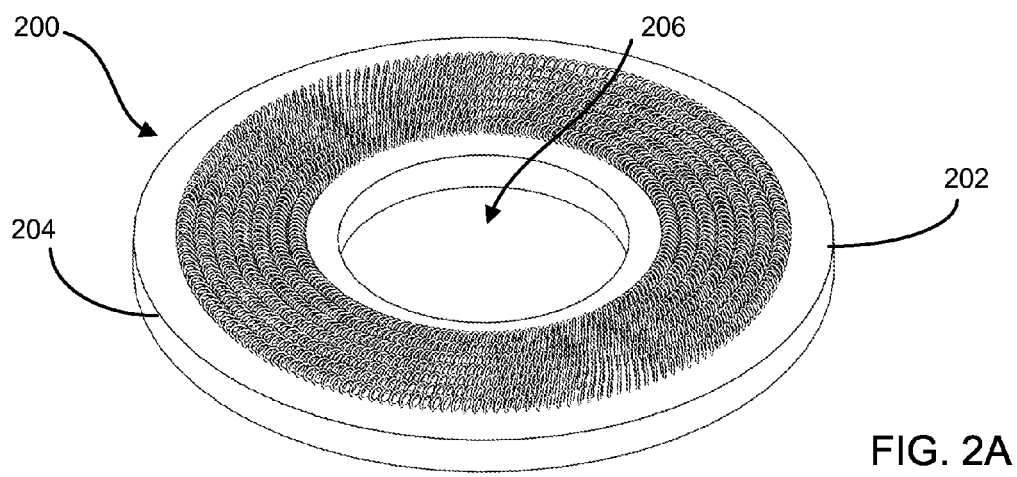
FIG. 2A is an oblique view of another embodiment of a percutaneous port.
Figure 2B:
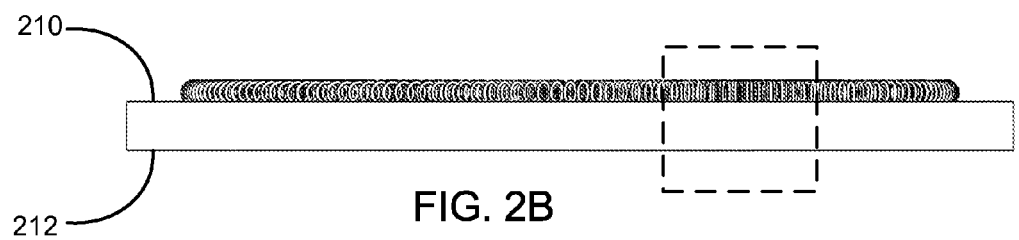
FIG. 2B is a side cross-sectional view of the percutaneous port shown in FIG. 2A.
Figure 2C:
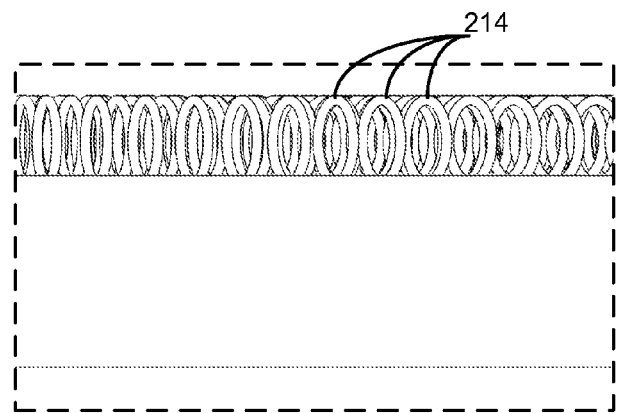
FIG. 2C is a close-up of the cross-sectional view shown in FIG. 2B.

FIGS. 2A-2C illustrate multiple views of another embodiment of a percutaneous port 200. Specifically, FIG. 2A is an oblique view of the percutaneous port 200; FIG. 2B is a side cross-sectional view of the percutaneous port shown in FIG. 2A; and FIG. 2C is a close-up of the cross-sectional view shown in FIG. 2B.

The percutaneous port 200 includes a substrate or plate 202 with coil 204 joined to one surface thereof. More specifically, the plate 202 defines a hole 206 therein (e.g., a first opening) and first and second opposing and substantially planar surfaces 210 and 212 (FIG. 2B), respectively. At least a portion of an outer surface of the coils 104 is joined to at least a portion of the first surface 210 of the plate 202 through any suitable technique, such as brazing. As shown, the coil 104 includes a plurality of loops 214. As described above with respect to the percutaneous port 100 of FIGS. 1A-1C, the plurality of loops 214 of the coil 204 facilitate optimal tissue in-growth, enabling a stronger physical integration of the percutaneous port 200 with the surrounding tissue, thereby mitigating issues such as inadvertent port removal and infection.

The percutaneous port 200 provides an interface enabling internal access to a patient in which a percutaneous port 200 is implanted. As described above with respect to the percutaneous port 100 of FIGS. 1A-1C, the opening 206 provides a port through which external components (e.g., electronic devices) can access internal components (e.g., implanted sensors). The flat percutanous port reduces the vertical dimension of the port.

The plate 202 can have any suitable shape, such as the disc shape shown in the figures. In other embodiments, the plate 202 is square, rectangular, or polygonal. Furthermore, in some embodiments, the plate 202 is made from titanium or any other suitable material. In some embodiments, the first surface 210 of the plate 202 is made from a material selected from nickel or any other suitable material.

The coil 204 is the same as coil 104 discussed above in relation to the percutaneous port 100. The longitudinal axis in this embodiment is formed through the center opening of the plate 202 and is perpendicular to the first surface 210 of the plate 202.

In some embodiments, the coil 204 is arranged such that it forms a spiral around the opening 206. In some embodiments, an additional coil (not shown), as discussed above in relation to the percutaneous port 100, having a distinct loop diameter from the coil 204, forms a separate spiral around the plate 202. In this embodiment, the separate spiral is interleaved with the spiral of the coil 204. Furthermore, in some embodiments, as shown in FIG. 2C, the loops of the coil(s) at least partially overlap with one another. Alternatively, in some embodiments, the coil 204 is arranged as an array (e.g., a grid pattern) along the first surface 210 of the plate 202. In yet other embodiments, the multiple coils 214 are arranged in straight lines radiating outward from the opening 206.

FIGS. 3A-3D illustrate a flowchart representing a method 300 of manufacturing a percutaneous port, in accordance with some embodiments. The method 300 primarily discusses manufacture of the percutaneous port 100 described in relation to FIGS. 1A-1C, however, a similar process can also be used for manufacturing the percutaneous port 200 of FIGS. 2A-2C. Throughout the description of the method 300, reference will be made to FIGS. 4A-4N, which are perspective views of the percutaneous port 100 being manufactured, i.e., during various stages of manufacture. It should be noted that while FIGS. 4A-4N show views of the percutaneous port 100 during manufacture, method 300 is not limited to such and also applies to the manufacture of the percutaneous port 200.

In some embodiments, a manufacturing device (e.g., machinery including a brazing fixture 400, FIG. 4B) is coupled to a computer control system (not shown) for facilitating the manufacture of a percutaneous port. The computer control system includes a processor (not shown) and memory (not shown) storing instructions for performing the method 300.

Figure 3A:
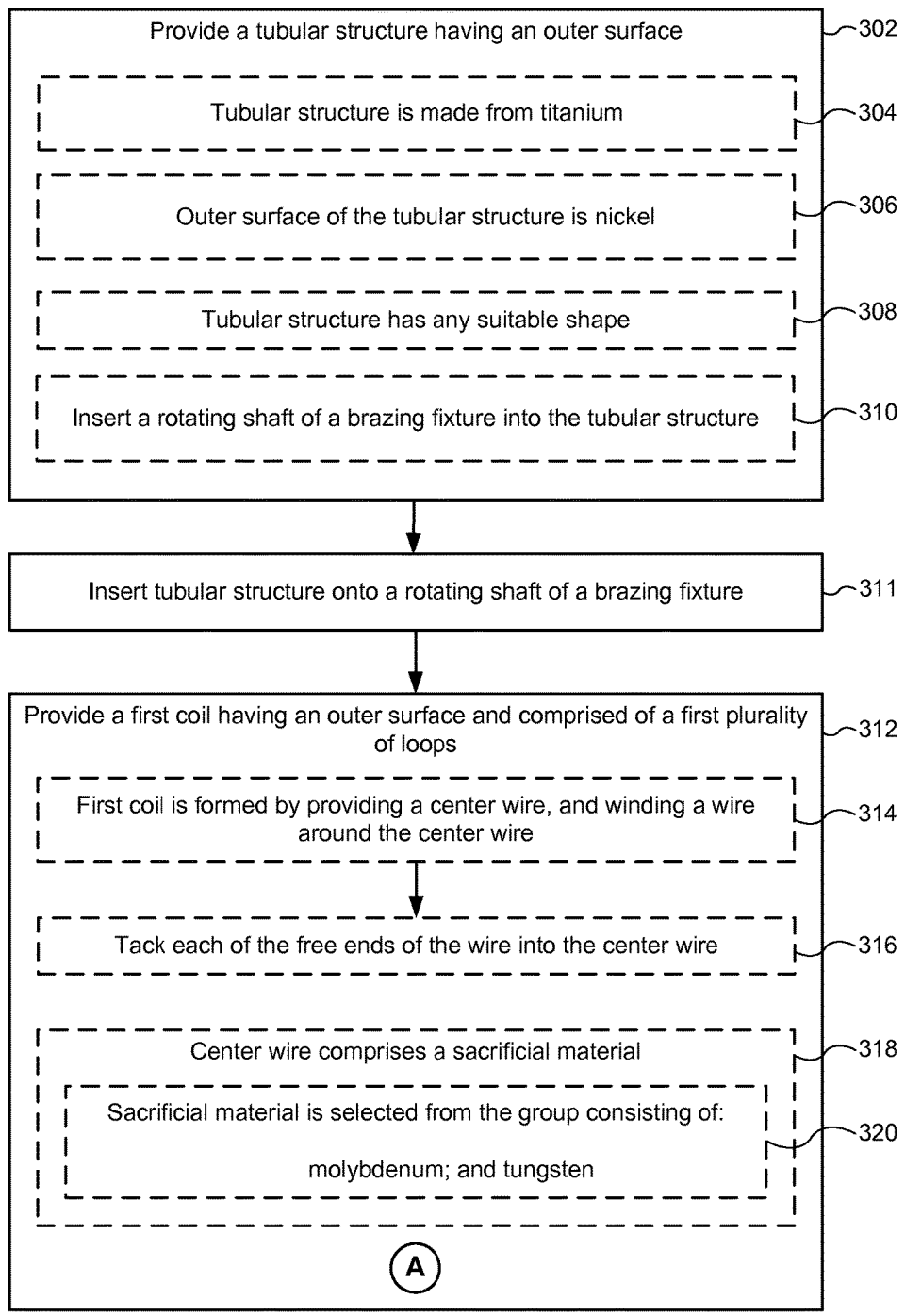
FIGS. 3A-3D are flowcharts of a method of manufacturing a percutaneous port, in accordance with some embodiments.
Figure 3B:
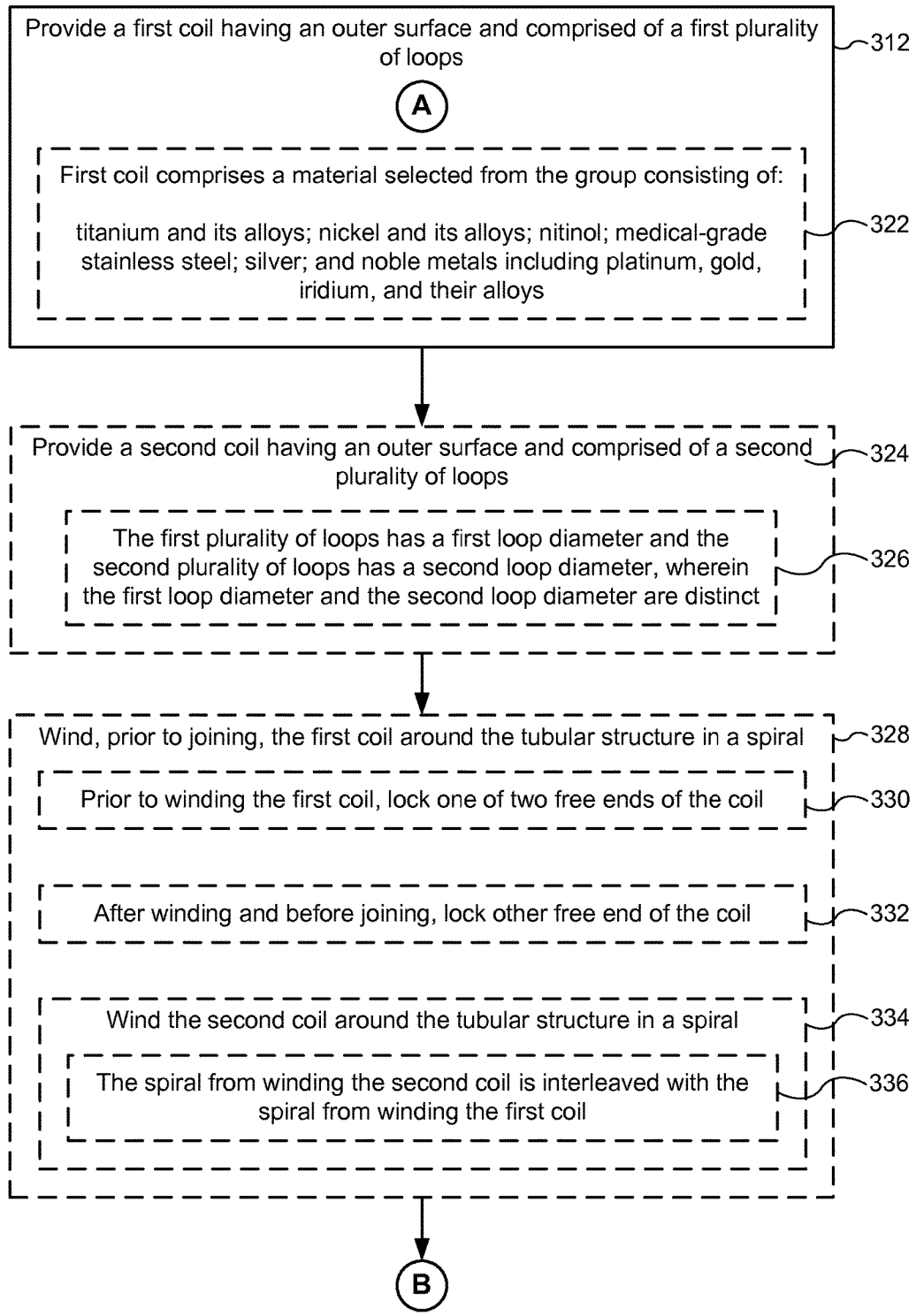
Figure 3C:
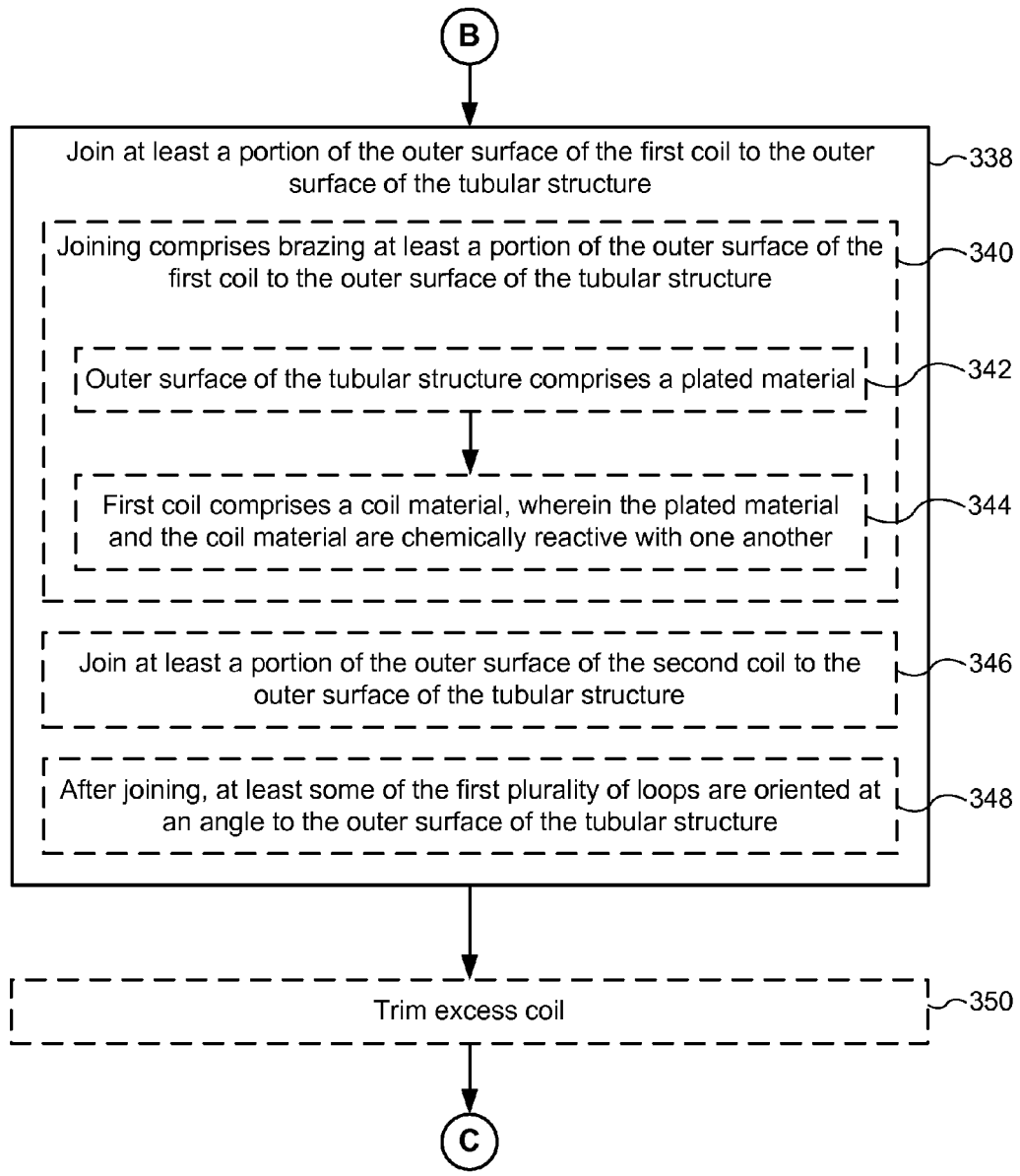
Figure 3D:
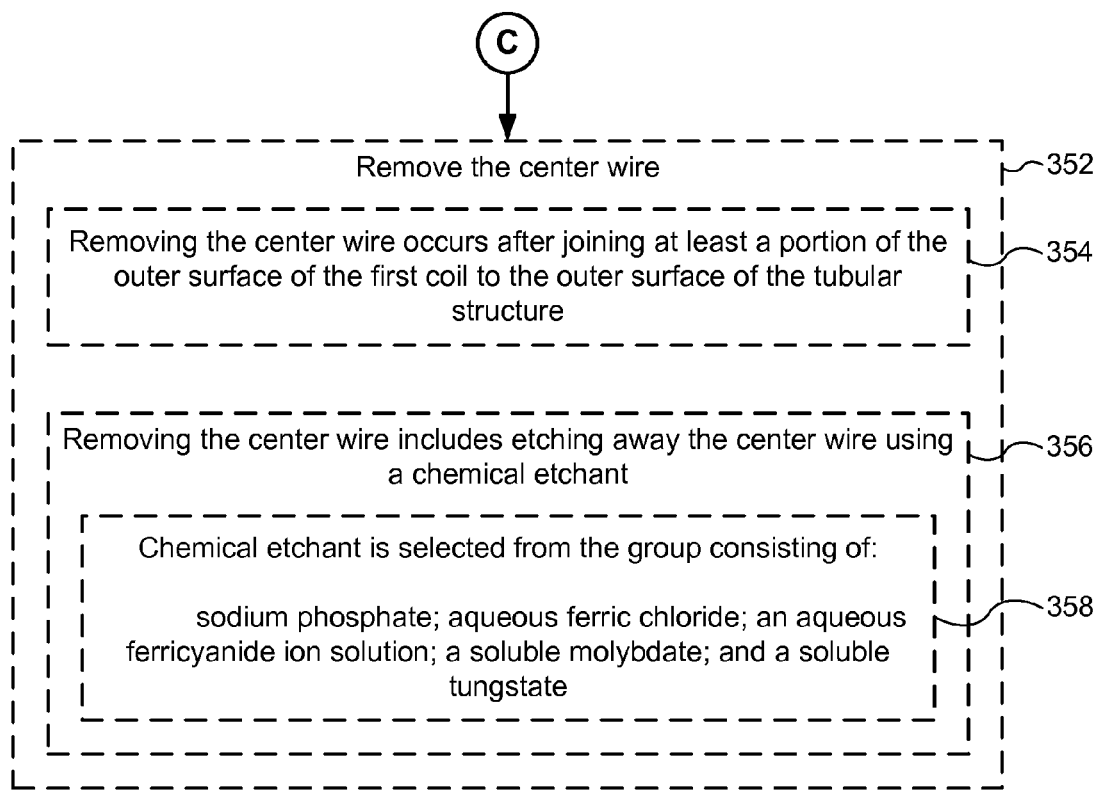
Figure 4A:
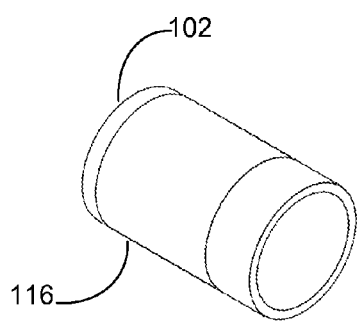
FIGS. 4A-4N are perspective views of a percutaneous port during various stages of manufacture, in accordance with some embodiments.

Initially, as shown in FIG. 3A, a tubular structure having an outer surface is provided (302). FIG. 4A shows a perspective view of the tubular structure 102 with the outer surface 116(*b*). A non-limiting example of a tubular structure 102 is also shown in FIGS. 1A-1C. As described above, in some embodiments, the tubular structure 102 includes an outer surface 116(*b*) to which the coils 104 and/or 118 are joined. In some embodiments, the tubular structure 102 is made (304) from titanium. In some embodiments, the outer surface 116 of the tubular structure 102 is (306) nickel. Furthermore, although the tubular structure 102 is cylindrical in the example provided, in some embodiments, the tubular structure 102 has (308) any suitable shape. Various other features and aspects of the tubular structure 102 and the outer surface 116 are described in greater detail above with respect to FIGS. 1A-1C.

Figure 4B:
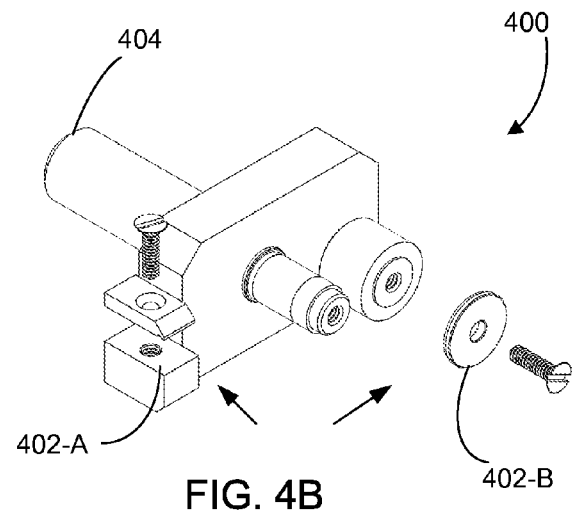
Figure 4C:
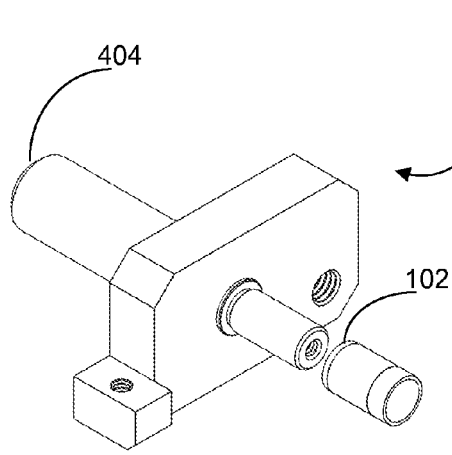
Figure 4D:
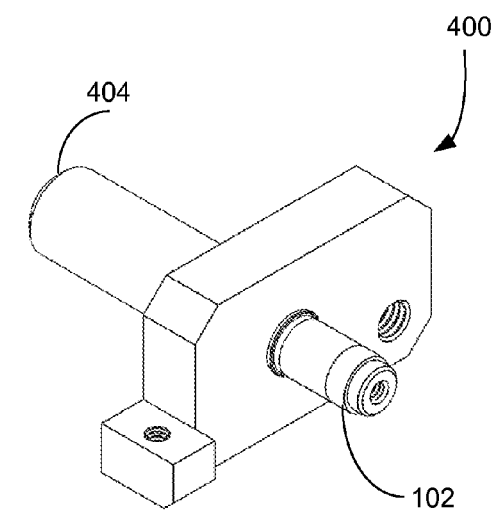

In some embodiments, the tubular structure 102 is inserted (311) onto a rotatable shaft of a brazing fixture. An example of a brazing fixture 400 is shown in FIG. 4B. In some embodiments, the brazing fixture 400 includes one or more locking mechanisms 402-A, 402-B (e.g., for locking the free ends of the coil 104, FIG. 4K prior to the winding and after the joining steps, as discussed below), and a rotatable shaft 404. As shown in FIGS. 4C and 4D, the rotatable shaft 404 of the brazing fixture 400 is inserted into the tubular structure 102.

Figure 4E:
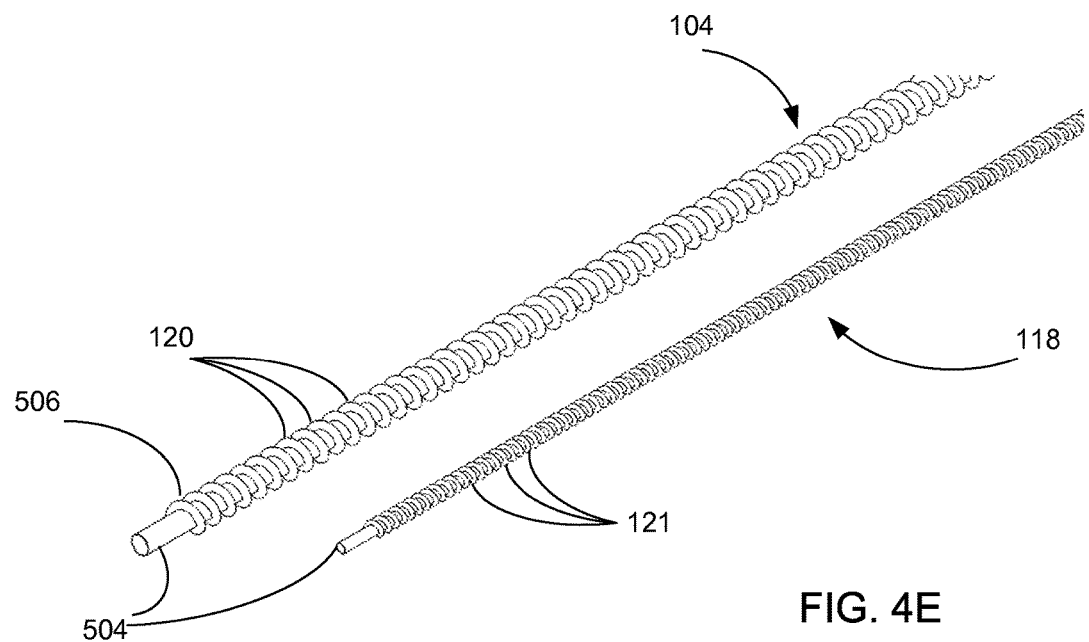

Next, a coil having an outer surface and comprised of a plurality of loops is provided (312). A non-limiting example of a coil 104 is shown in FIG. 4E. In some embodiments, the coil 104 is formed (314) by providing a center rod 504, and winding a wire (e.g., which comprises the coil 104) around the center rod 504. Afterwards, in some embodiments, each of the free ends of the wire is tacked (316) into the center rod 504. FIG. 4E illustrates the coil 104 formed by a center rod 504, around which a wire (e.g., which comprises the coil 104) is wound in a spiral fashion, where the ends 506 of the wire are tacked into the center rod 504. In some implementations, the ends 506 of the wire are laser tacked into the center rod 504. In some embodiments, the center rod 504 comprises (318) a sacrificial material. Specifically, in some embodiments, the sacrificial material is selected (320) from the group consisting of: molybdenum and tungsten. As described in greater detail below, in some embodiments, the center rod 504 is later etched away using a chemical etchant to form the coil 104 shown in FIG. 1A. In some embodiments, the coil comprises (322) a material selected from the group consisting of: titanium and its alloys, nitinol, tungsten and its alloys, molybdenum and its alloys, niobium and its alloys, cobalt-chromium based alloys, noble metals, such as platinum, iridium, palladium, silver, gold, and their alloys, and medical grade stainless steel.

In other embodiments, the coil 104 shown in FIG. 1A is formed by a method not requiring the use of a chemical etchant and a center rod consisting of a sacrificial material. For example, in some embodiments, a coil 104 is formed by twisting and/or bending a wire (e.g., a wire comprising the coil 104). Alternatively, rather than providing a coil comprised of a plurality of loops, some embodiments include providing a plurality of individual, unconnected rings for joining to the outer surface 116 of the tubular structure 102.

As described in greater detail above with respect to FIGS. 1A-1C, the plurality of loops of the coil has a loop diameter. In some embodiments, the loop diameter is controlled by the diameter of the center rod 504. Furthermore, in some embodiments, the center rod 504 has a non-circular shape (e.g., polygonal), which also defines the shape of the plurality of loops. Various other features and aspects of the plurality of loops are described in greater detail above with respect to FIGS. 1A-1C and 2A-2C.

In some embodiments, an additional coil having an outer surface and comprised of a plurality of loops (e.g., loops 121) is provided (324). Furthermore, in some embodiments, the plurality of loops of the coil has a first loop diameter and the plurality of loops of the additional coil has a second loop diameter, wherein the first loop diameter and the second loop diameter are distinct (326). An example of such an embodiment is shown in FIG. 4E, which illustrates the coil (e.g., coil 104) and the additional coil (e.g., coil 118), wherein their respective plurality of loops have distinct loop diameters from one another. In some embodiments, the additional coil (e.g., additional coil 118) is wound around the coil (e.g., coil 104).

Figure 4F:
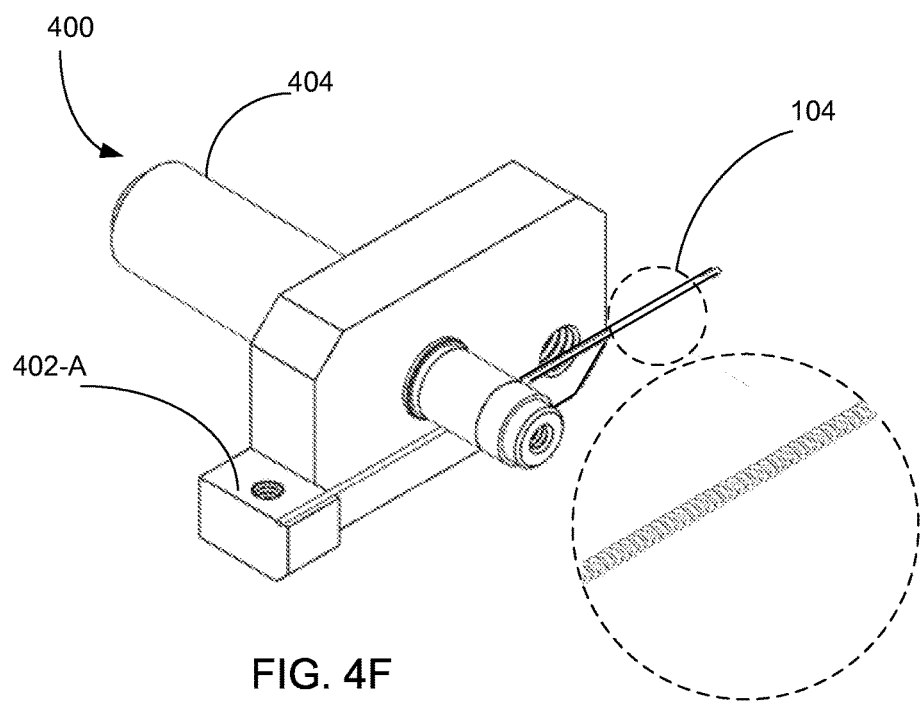
Figure 4G:
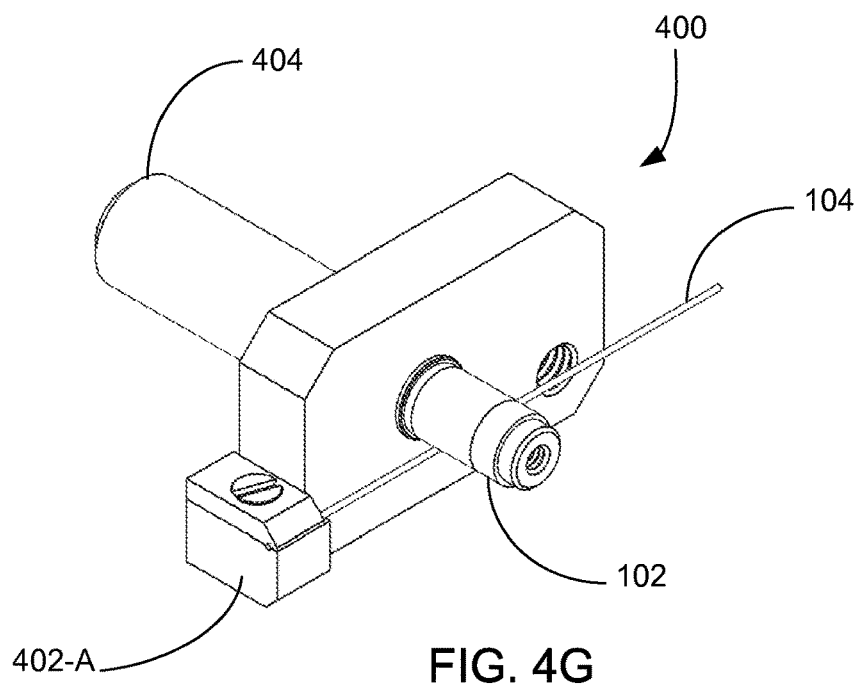
Figure 4H:
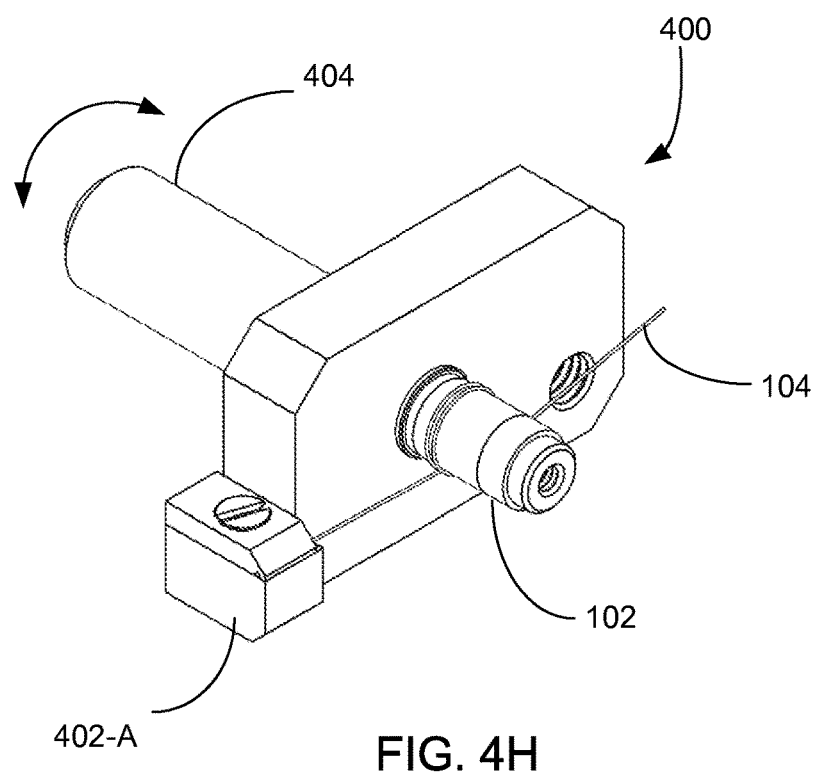
Figure 4I:
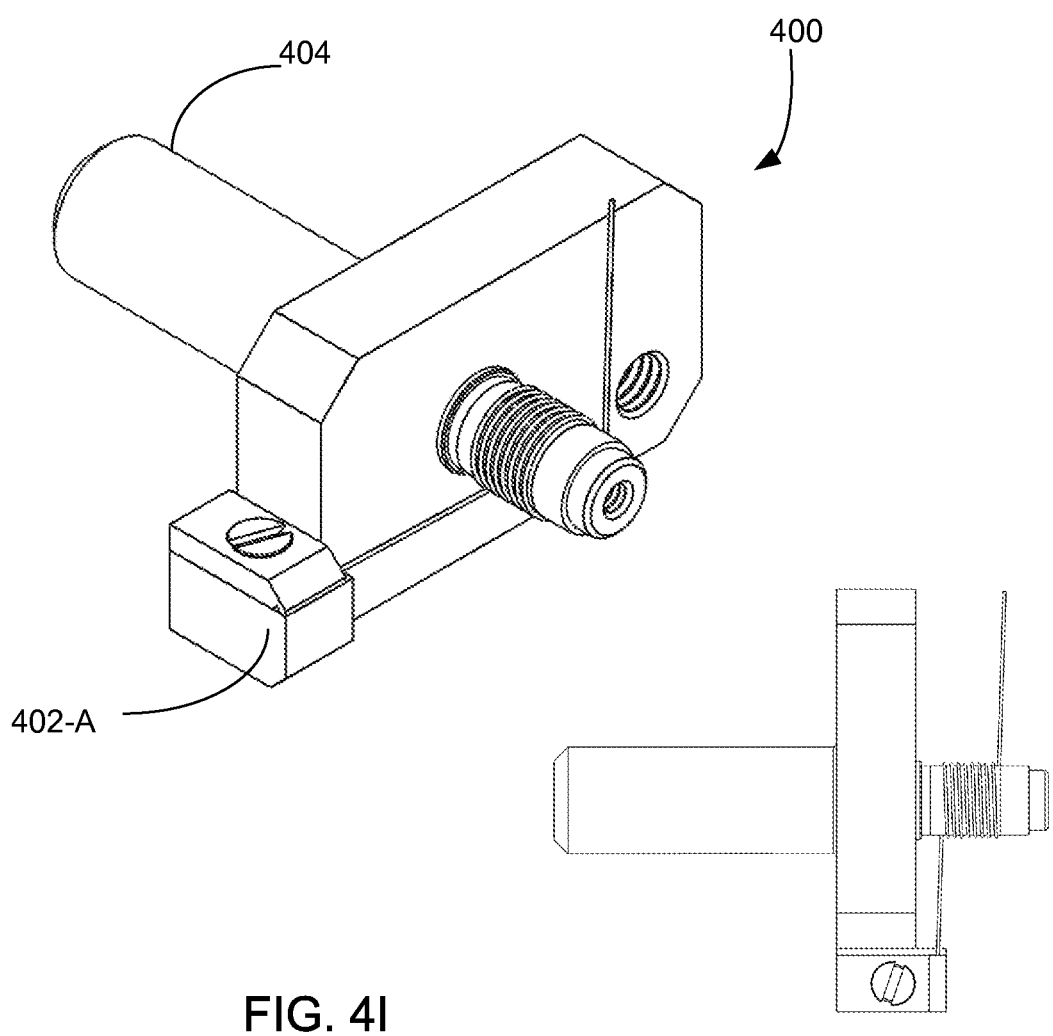
Figure 4J:
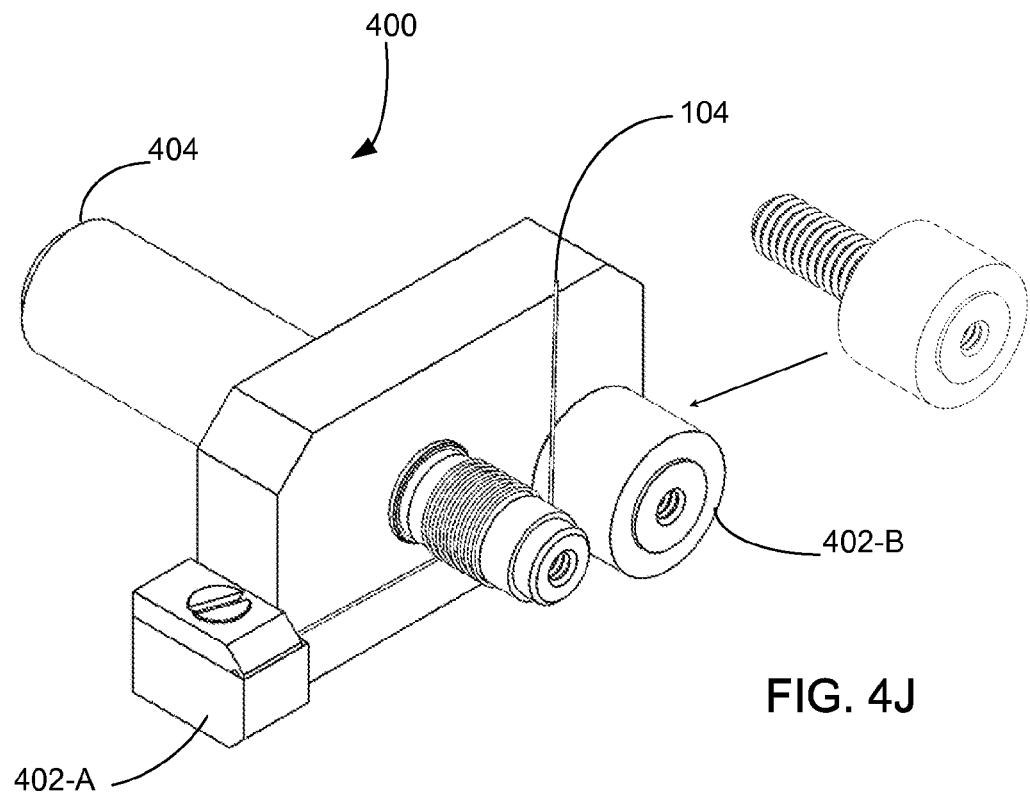
Figure 4K:
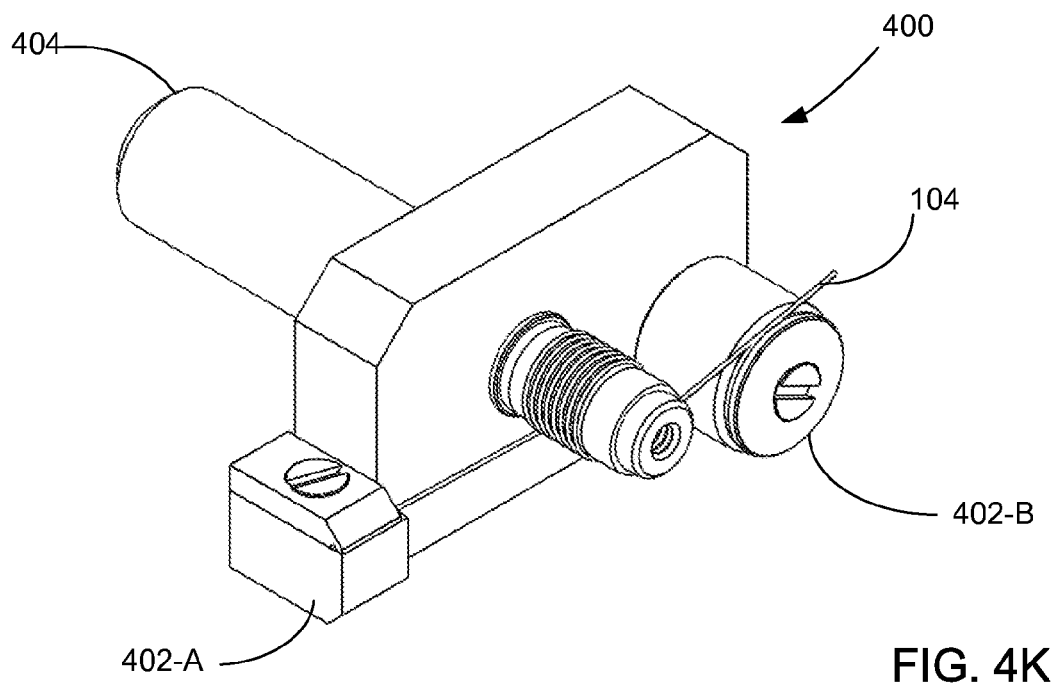
Figure 4L:
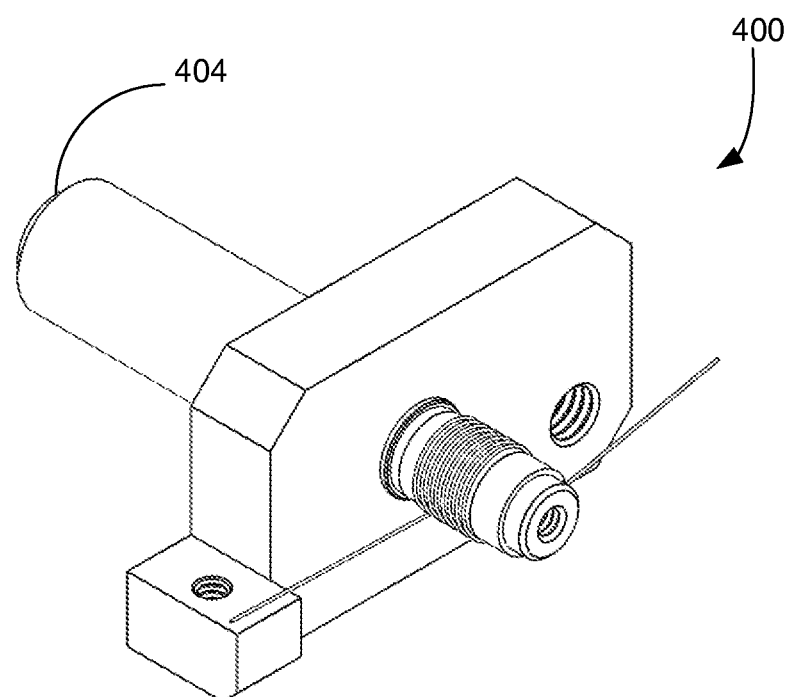
Figure 4M:
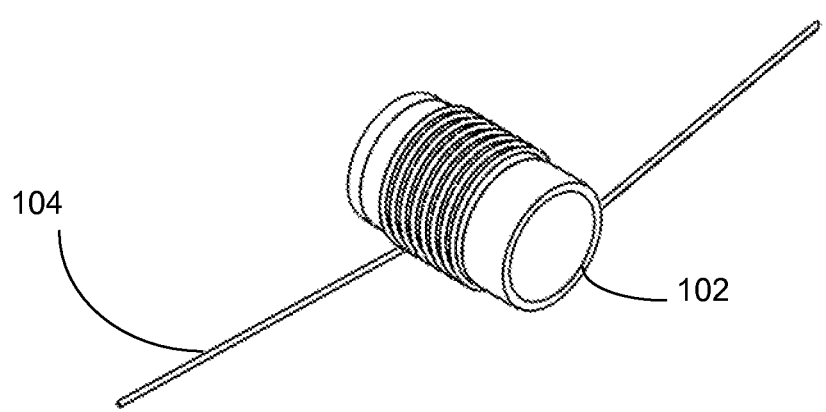
Figure 4N:
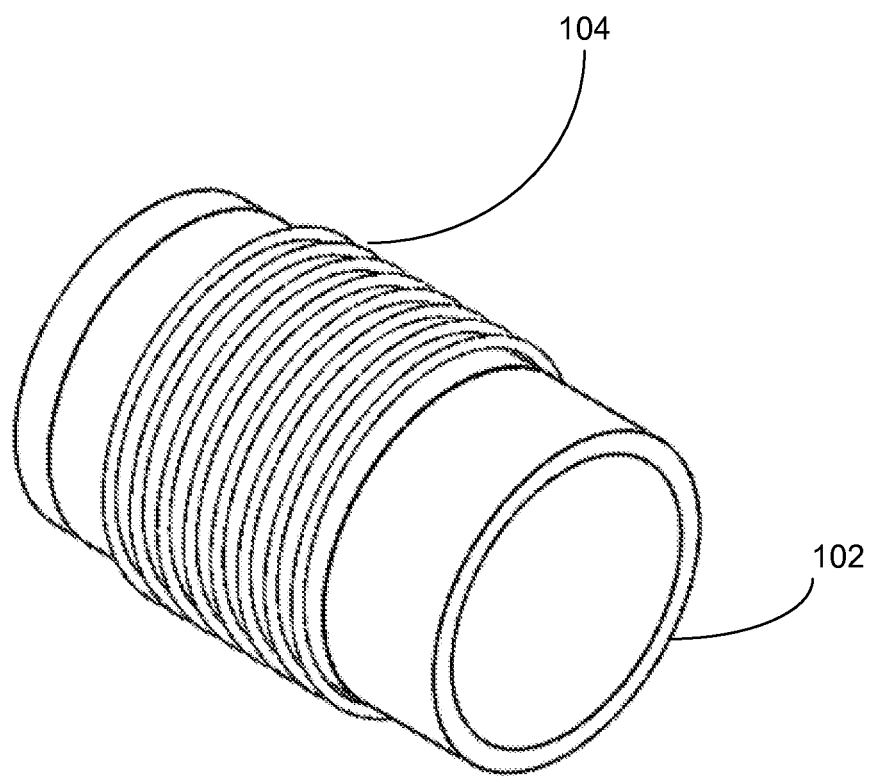

Optionally, in some embodiments, prior to joining at least a portion of the outer surface of the coil to the outer surface of the tubular structure 102 (as described in greater detail below), the coil is wound (328) around the tubular structure 102 in a spiral. FIGS. 4F-4K illustrate this process in greater detail. First, in some embodiments, prior to winding the coil, one of two free ends of the coil are locked in a fixed position. For example, as shown in FIG. 4F, the coil 104 is positioned into the locking mechanism 402-A of the brazing fixture 400, and in FIG. 4G, the coil 104 is locked (330) in a fixed position (e.g., using a screw to tighten a clamp). Next, as shown in FIGS. 4H and 4I, the coil is wound around the tubular structure 102 in a spiral. In FIG. 4H, for example, by rotating the shaft 404 of the brazing fixture 400 inserted into the tubular structure 102, the shaft 404 (e.g., coupled to and powered by a motor) rotates in either a clock-wise or counter-clock-wise direction, such that the coil 104 forms a spiral around the tubular structure 102. In some implementations, while the shaft 404 rotates, tension is simultaneously applied to the free end of the coil 104. In some implementations, the coil 104 is wound around the tubular structure 102 until a predetermined unwound length of the coil 104 remains. For example, as shown in FIG. 4M, after the coil 104 has been wound around the tubular structure 102, an unwound excess length of the coil 104 remains un-joined to the tubular structure 102.

In some embodiments, the coil is arranged along the longitudinal axis of the tubular structure 102. In other embodiments, a plurality of individual, unconnected loops are arranged (e.g., in an array or other predefined pattern) along the outer surface of the tubular structure 102.

In some implementations, after winding the coil, but before joining at least a portion of the outer surface of the coil to the outer surface of the tubular structure 102, the other free end of the coil is locked (332) in a fixed position. As shown in the examples of FIGS. 4J and 4K, after winding the coil 104 around the tubular structure 102, the remaining free end of the coil 104 is locked into the locking mechanism 402-B (e.g., using a screw to tighten a clamp) in preparation for a joining process, as described in greater detail below.

In some embodiments, the additional coil is wound (334) around the tubular structure 102 in a spiral. As described in greater detail above, in some embodiments, the spiral from winding the additional coil is interleaved (336) with the spiral from winding the coil. FIG. 1C illustrates an example in which the distinct spirals from winding the coil and the additional coil are interleaved. In some embodiments, both the coil and the additional coil are simultaneously wound around the tubular structure 102.

After providing the tubular structure 102 and the coil, at least a portion of the outer surface of the coil is joined (338) to the outer surface of the tubular structure 102.

In some embodiments, the joining comprises brazing (340) at least a portion of the outer surface of the coil to the outer surface of the tubular structure 102. Brazing is a process by which two components are joined together by heating a material (e.g., which is sometimes the material of the components themselves) above its melting point. Implementations sometimes use a brazing oven, which provides an inert environment (e.g., gas or vacuum) in which the brazing process is carried out. The example provided in FIGS. 4-7 illustrate such a brazing process and the preparation involved. Specifically, after the coil 104 has been wound around the tubular structure 102 and its free ends locked into place, the entire brazing fixture 400 containing the unfinished percutaneous port assembly (FIG. 4K) is placed into a brazing oven. In some embodiments, the brazing fixture 400 is made of a high temperature alloy (e.g., alloy 42 or 50) so that it can withstand the high temperatures of the brazing process. In the example shown, while applying the high brazing temperature to the unfinished percutaneous port assembly, at least a portion of the outer surface of the coil 104 and the outer surface 116 are brought to or above their melting point and thus bonded together. In some embodiments, the outer surface of the tubular structure 102 comprises (342) a plated material, and the coil comprises (344) a coil material, wherein the plated material and the coil material are chemically reactive with one another. Examples of such materials are described above with respect to FIGS. 1A-1C.

In some implementations, brazing is performed for a predefined period of time that is based at least in part on a thickness of the wire comprising the coil (e.g., coil 104), a thickness of the outer surface (e.g., outer surface 116, FIG. 1A) of the tubular structure, and the predefined brazing temperature. For example, the predefined brazing temperature is typically within the range of 940 degrees Celsius to 1050 degrees Celsius, with a holding time between 1 to 60 minutes. As shown in FIGS. 4L and 4M, after applying the high temperature for a predefined period of time, the locking mechanisms are unlocked and the brazed percutaneous port assembly is removed from the brazing fixture. FIG. 4N illustrates a brazed percutaneous port assembly with the center rod of the coil still intact. The percutaneous port 100 of FIG. 1A is an example of a finished percutaneous port after the center rod 504 is removed (described below).

In other embodiments, the joining comprises a welding process, such as resistance welding, laser welding and e-beam welding, whereby the coil is welded to the outer surface of the tubular structure 102. Alternatively, in some embodiments, joining comprises using a medical grade epoxy to bind the coil to the outer surface of the tubular structure 102. In some embodiments, joining comprises using soldering or solid state diffusion.

In some embodiments, at least a portion of the outer surface of the additional coil is joined (346) to the outer surface of the tubular structure 102, in a similar manner to that described above for joining the coil 104 to the tubular structure 102.

In some embodiments, after the joining, at least some of the plurality of loops are oriented (348) at an angle to the outer surface of the tubular structure 102. Loop orientation is described in greater detail above with respect to FIGS. 1A-1C.

In some embodiments, after the joining, any excess or remaining coil is trimmed (350). For example, as shown in FIG. 4M, the excess coil that was not joined to the outer surface of the tubular structure 102 is trimmed off.

In some embodiments in which a center rod is used to form the coil, the center rod is then removed (352). In some embodiments, removing the center rod (e.g., center rod 504) occurs (354) after joining at least a portion of the outer surface of the coil to the outer surface of the tubular structure 102, while in other embodiments, the center rod is removed before the joining In some embodiments, removing the center rod includes (356) etching away the center rod using a chemical etchant. For example, the brazed percutaneous port assembly, with the center rod still intact (FIG. 4N), is placed into a chemical etchant solution, which reacts with and dissolves only the sacrificial material of the center rod, leaving the tubular structure 102 and the coil 104 intact. In some embodiments, the chemical etchant is selected (358) from the group consisting of: sodium phosphate; aqueous ferric chloride; an aqueous ferricyanide ion solution; a soluble molybdate; and a soluble tungstate.

It should be understood that the particular order in which the operations in FIGS. 3A-3D have been described is merely exemplary and is not intended to restrict the method 300 to the order described. One of ordinary skill in the art would recognize various ways to reorder the operations described herein.

It will be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific implementations. However, the illustrative discussions above are not intended to be exhaustive or to limit the claims to the precise forms disclosed. Many modifications and variations are possible in view of the above teachings. The implementations were chosen and described in order to best explain principles of operation and practical applications, to thereby enable others skilled in the art.

What is claimed is:

1. A method of manufacturing a percutaneous port for promoting tissue in-growth around the percutaneous port, comprising:
    providing a tubular structure having an outer surface;
    providing a continuous coil having an outer surface and comprised of a plurality of loops, the coil formed by:
        providing a center rod; and
        winding a wire around the center rod;
    winding the coil around the tubular structure in a spiral; and
    joining at least a portion of the outer surface of the coil to the outer surface of the tubular structure, wherein the center rod is removed after the joining.

2. The method of claim 1, wherein after the joining, at least some of the loops of the coil are oriented at an angle to the outer surface of the tubular structure.

3. The method of claim 2, wherein the angle to the outer surface of the tubular structure is substantially perpendicular.

4. The method of claim 2, wherein the at least some of the loops of the coil are further oriented at an angle substantially parallel to the longitudinal axis of tubular structure.

5. The method of claim 1, wherein joining comprises brazing at least a portion of the outer surface of the coil to the outer surface of the tubular structure.

6. The method of claim 5, wherein brazing is performed for a predefined period of time that is based at least in part on a thickness of the wire comprising the coil, a thickness of the outer surface of the tubular structure, and a predefined brazing temperature.

7. The method of claim 1, wherein removing the center rod includes etching away the center rod using a chemical etchant.

8. The method of claim 7, wherein the center rod is selected from the group consisting of molybdenum and tungsten, and wherein the chemical etchant is selected from the group consisting of sodium phosphate, aqueous ferric chloride, an aqueous ferricyanide ion solution, a soluble molybdate, and a soluble tungstate.

9. The method of claim 1, further comprising:
    providing an additional coil having an outer surface and comprised of a plurality of loops;
    winding the additional coil around the tubular structure in a spiral; and
    joining at least a portion of the outer surface of the additional coil to the outer surface of the tubular structure,
    wherein the loops of the coil have a first diameter and the loops of the additional coil have a second diameter, wherein the first diameter is significantly larger than the second diameter.

10. The method of claim 9, wherein the additional coil is interleaved between the coil.

11. The method of claim 1, wherein:
    the outer surface of the tubular structure comprises a plated material; and
    the coil comprises a coil material, wherein the plated material and the coil material are chemically reactive with one another.

12. The method of claim 1, wherein the coil comprises a material selected from the group consisting of titanium and its alloys, nitinol, tungsten and its alloys, molybdenum and its alloys, niobium and its alloys, cobalt-chromium based alloys, noble metals and their alloys, and medical grade stainless steel.

13. The method of claim 1, wherein the tubular structure is made from titanium, and the outer surface of the tubular structure is made from nickel.

14. The method of claim 1, wherein the longitudinal axis of the coil is substantially parallel to the longitudinal axis of the tubular structure.

15. The method of claim 1, wherein a predefined spacing between adjacent loops in the coil is variable.

16. The method of claim 1, wherein the tubular structure is cylindrical.

17. The method of claim 1, wherein the tubular structure is not cylindrical.

* * * * *

UNITED STATES PATENT AND TRADEMARK OFFICE
CERTIFICATE OF CORRECTION

PATENT NO. : 10,086,184 B2
APPLICATION NO. : 14/877857
DATED : October 2, 2018
INVENTOR(S) : Jiang et al.

Page 1 of 1

It is certified that error appears in the above-identified patent and that said Letters Patent is hereby corrected as shown below:

In the Specification

Column 11, Line 39, please delete "4-7 illustrate" and insert --4A-4N illustrate--.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*